United States Patent
Ahmed et al.

(10) Patent No.: US 11,970,440 B1
(45) Date of Patent: *Apr. 30, 2024

(54) 8-(3-CHLOROBENZYLIDENEAMINO) NAPHTHALENE-1,3-DISULFONIC ACID AS AN ANTIOXIDANT COMPOUND

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Antar Ahmed Abdelhamid Ahmed, Sohag (EG); Amer A. Amer, Sohag (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/385,216

(22) Filed: Oct. 30, 2023

(51) Int. Cl.
*C07C 309/47* (2006.01)
*A61P 39/06* (2006.01)

(52) U.S. Cl.
CPC .......... *C07C 309/47* (2013.01); *A61P 39/06* (2018.01)

(58) Field of Classification Search
CPC ........................ C07C 309/47; C07C 303/22
See application file for complete search history.

(56) References Cited

U.S. PATENT DOCUMENTS 3,773,827 A   11/1973   Schundehutte
6,214,996 B1   4/2001   Ukita et al.

FOREIGN PATENT DOCUMENTS

EP   0138303 A1   4/1985

OTHER PUBLICATIONS

Letunove et al, Synthesis of derivatives of benzo[h]quinolines by condensation of Schiff bases with ketones, 1984, STN record of Zhurnal Organicheskoi Khimii, vol. 20, No. 1, Doc No. 100:191715, p. 1-2 (Year: 1984).*
NPL-1: "8-{(E)-[(4-Chlorophenyl)Methylidene]Amino} Naphthalene-1-Sulfonic Acid".
NPL-2: "8-{(E)-[(4-Chlorophenyl)Methylidene]Amino} Naphthalene-1-Sulfonic Acid".
NPL-3: "8-[(E)-Benzylideneamino]Naphthalene-1-Sulfonic Acid".
NPL-4: "N-(2-Naphthyl)-3-Chlorobenzenemethaneimine".
NPL-5: Zoubi et al., "Acyclic And Cyclic Imines And Their Metal Complexes: Recent Progress In Biomaterials And Corrosion Applications", RSC Adv. Jun. 21, 2018; 8(41): 23294-23318.
NPL-6: Ibrahim et al., "Synthesis And Antibacterial Activities Of Some Schiff Bases", Journal of Chemistry, vol. 8, 2011.

* cited by examiner

*Primary Examiner* — Samantha L Shterengarts
*Assistant Examiner* — Karen Cheng
(74) *Attorney, Agent, or Firm* — Nath, Goldberg & Meyer; Richard C. Litman

(57) ABSTRACT

An 8-(3-chlorobenzylideneamino)naphthalene-1,3-disulfonic acid compound, its synthesis, and its use as an antioxidant agent.

7 Claims, No Drawings

8-(3-CHLOROBENZYLIDENEAMINO) NAPHTHALENE-1,3-DISULFONIC ACID AS AN ANTIOXIDANT COMPOUND

BACKGROUND

1. Field

The present disclosure relates to a 8-(3-chlorobenzylideneamino)naphthalene-1,3-disulfonic acid compound, its synthesis, and its use as an antioxidant agent.

2. Description of the Related Art

There remains an ongoing need for new therapeutically active agents for treating a variety of diseases, disorders, and conditions including, but not limited to, various forms of cancer, various microbial infections, and the like.

Bacterial infection remains a significant threat to human life due to its increasing resistance to conventional antibiotics, which is a growing public health concern. As a result, there is a critical need to create new antimicrobial agents with activity against potent anti-drug-resistant microorganisms.

Schiff bases are a kind of organic dye generally characterized by their nitrogen-carbon double bond (—N=C—). Schiff bases, especially those linked with a heterocyclic moiety, have exhibited various pharmacological and biological activities such as antibacterial, cytotoxic effects, antifungal, antimalarial, anticonvulsant, antioxidant, and anti-inflammatory activities. In addition, there are some market drugs bearing a heterocyclic Schiff base, e.g., Dantrolene®, Nitrofurantoin®, and Nifurtimox®. Nowadays, the synthesis of Schiff base compounds has gained particular attention due to their potent bioactivities.

The sulfonic acid group represents a key structural motif in both synthetic and medicinal chemistry. Many compounds containing sulfonic acid groups are well known as antibacterial, antifungal and antitubercular agents. Additionally, compounds containing sulfonic acid groups can be used as dyes.

In recent years, there has been a tremendous upsurge of interest in various chemical transformations performed under ultrasound irradiation. However, with using ultrasound irradiation, chemical transformations can occur, with higher yields and purity of the products, shorter reaction times, and milder conditions, that create economic advantages. This greener method is crucial to reduce the negative impact of traditional methods. Hence, the ultrasound technique is a green chemistry technique that is quicker and healthier than conventional methods.

Thus, new molecules having desired therapeutic activities and solving the aforementioned problems are desired.

SUMMARY

The product described herein is a new Schiff base derivative produced in order to provide a limited library of "drug-like" substances. 8-(3-chlorobenzylideneamino)naphthalene-1,3-disulfonic acid (III) was synthesized by reaction between 8-aminonaphthalene-1,3-disulfonic acid (I) and 3-chlorobenzaldehyde (II) in the presence of triethylamine as a basic catalyst, using an ultrasonic (U/S) technique as a source of heat as an eco-friendly method.

The compound 8-(3-chlorobenzylidene amino)naphthalene-1,3-disulfonic acid is not only new but demonstrated excellent antioxidant activities. The antioxidant activity of 8-(3-chlorobenzylideneamino)naphthalene-1,3-disulfonic acid was investigated by 2,2-diphenyl-1-picrylhydrazyl (DPPH) in vitro tests that employ vitamin C as the positive control. The test indicated the product III had an estimated antioxidant potential to vanish the DPPH radical distinctive colors at 517 nm. The results showed that the compound III has a high potential as an antioxidant compared to vitamin C by antioxidant molecules donating hydrogen to a free radical, removing the extra electron and vanishing the DPPH radical distinctive colors.

In an embodiment, the present subject matter relates to a 8-(3-chlorobenzylideneamino)naphthalene-1,3-disulfonic acid compound having the formula I:

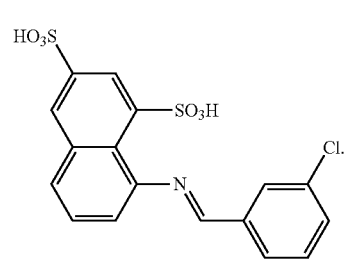

In another embodiment, the present subject matter relates to a pharmaceutically acceptable composition comprising a therapeutically effective amount of the 8-(3-chlorobenzylideneamino)naphthalene-1,3-disulfonic acid compound and a pharmaceutically acceptable carrier.

In an additional embodiment, the present subject matter relates to a method of producing an antioxidant effect in a patient comprising administering to a patient in need thereof a therapeutically effective amount of the 8-(3-chlorobenzylideneamino)naphthalene-1,3-disulfonic acid compound.

In one more embodiment, the present subject matter relates to a method of making the 8-(3-chlorobenzylideneamino)naphthalene-1,3-disulfonic acid compound, the method comprising: mixing 8-aminonaphthalene-1,3-disulfonic acid, 3-chlorobenzaldehyde, and triethylamine (TEA) in ethanol to obtain a solution; irradiating the solution followed by cooling to room temperature to obtain a formed precipitate; purifying the formed precipitate by filtering and recrystallization using ethanol; and obtaining the 8-(3-chlorobenzylideneamino)naphthalene-1,3-disulfonic acid compound.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as providing an antioxidant effect.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The compound 8-(3-chlorobenzylideneamino)naphthalene-1,3-disulfonic acid described herein is not only new but demonstrated excellent antioxidant activities. The antioxidant activity of 8-(3-chlorobenzylideneamino)naphthalene-1,3-disulfonic acid was investigated by 2,2-diphenyl-1-picrylhydrazyl (DPPH) in vitro tests that employ vitamin C as the positive control. The test indicated the product III had an estimated antioxidant potential to vanish the DPPH radical distinctive colors at 517 nm. The results showed that the compound III has a high potential as an antioxidant compared to vitamin C by antioxidant molecules donating hydrogen to a free radical, removing the extra electron and vanishing the DPPH radical distinctive colors.

In an embodiment, the present subject matter relates to an 8-(3-chlorobenzylideneamino)naphthalene-1,3-disulfonic acid compound having the formula I:

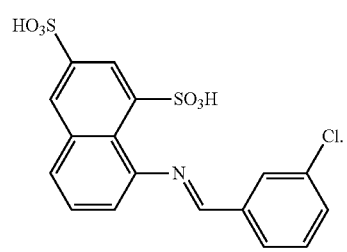

In a further embodiment, the 8-(3-chlorobenzylideneamino)naphthalene-1,3-disulfonic acid compound can have a melting point of about 221° C. to about 222° C.

In another embodiment, the present subject matter relates to a pharmaceutically acceptable composition comprising a therapeutically effective amount of the 8-(3-chlorobenzylideneamino)naphthalene-1,3-disulfonic acid compound and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide an antioxidant effect. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for providing an antioxidant effect, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols, or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum, and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In an additional embodiment, the present subject matter relates to a method of producing an antioxidant effect in a patient comprising administering to a patient in need thereof a therapeutically effective amount of the 8-(3-chlorobenzylideneamino)naphthalene-1,3-disulfonic acid compound.

In one more embodiment, the present subject matter relates to a method of making the 8-(3-chlorobenzylideneamino)naphthalene-1,3-disulfonic acid compound, the method comprising: mixing 8-aminonaphthalene-1,3-disulfonic acid, 3-chlorobenzaldehyde, and triethylamine (TEA) in ethanol to obtain a solution; irradiating the solution followed by cooling to room temperature to obtain a formed precipitate; purifying the formed precipitate by filtering and recrystallization using ethanol; and obtaining the 8-(3-chlorobenzylideneamino)naphthalene-1,3-di sulfonic acid compound.

The present production methods can be further seen by referring to the following Scheme 1:

Scheme 1

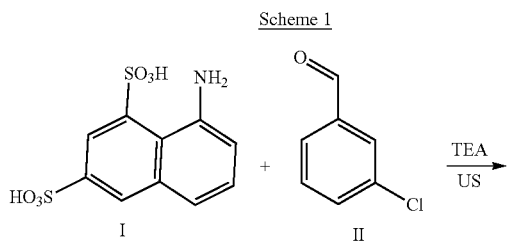

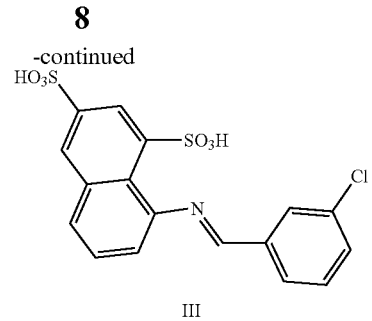

III

In an embodiment of the present production methods, the irradiating step can take place in a sonicator for at least about 2 hours. In another embodiment, the irradiating step can use ultrasonic (US) irradiation.

In another embodiment, the irradiating step can be conducted at about 45° C. to about 55° C., or at about 50° C.

In certain embodiments of the present production methods, the purifying step can include collecting the formed precipitate by filtration and washing the formed precipitate with distilled water.

In another embodiment of the present production methods, the mixing 8-aminonaphthalene-1,3-disulfonic acid and the 3-chlorobenzaldehyde may be added in about a 1:1 molar ratio.

In a further embodiment of the present production methods, the 8-(3-chlorobenzylideneamino)naphthalene-1,3-disulfonic acid compound can have a melting point of about 221° C. to about 222° C.

The following examples relate to various methods of manufacturing the specific compounds and application of the same, as described herein. All compound numbers expressed herein are with reference to the synthetic pathway figures shown above.

EXAMPLES

Example 1

Preparation of 8-(3-chlorobenzylideneamino)naphthalene-1,3-disulfonic acid

A solution of 8-aminonaphthalene-1,3-disulfonic acid (3.03 gm, 10 mmol), 3-chlorobenzaldehyde (II) (1.22 g, 10 mmol), and 3 drops of TEA in 50 ml ethanol was placed in a closed vessel and exposed to US irradiation for about 2 hours at 50° C. in a sonicator. After completion of the reaction (monitored with TLC), the reaction mixture was then cooled to room temperature. The formed precipitate was collected by filtration, washed by distilled water, dried, and crystallized from ethanol to give the desired 8-(3-chlorobenzylideneamino)naphthalene-1,3-disulfonic acid (III).

Characterization data for 8-(3-chlorobenzylideneamino) naphthalene-1,3-disulfonic acid (III):

Mp. 221-222° C. FTIR (KBr, cm$^{-1}$) 3057, (C—H arom.); $^1$H-NMR (DMSO-d6/D$_2$O, 400 MHz): 8.35 (s, 1H, N=CH), 7.35-7.20 (m, 5H, CHarom), 6.87-6.78 (m, 3H, CHarom), 6.60 (s, 1H, CHarom), 2.92 (br. s., 2H, 2SO$_3$H); C$_{17}$H$_{12}$ClNO$_6$S$_2$ (425.86); C, 47.95; H, 2.84; N, 3.29%. Found: C, 48.07; H, 2.75; N, 3.48%.

Example 2

Antioxidant Testing

Antioxidant Activity

The antioxidant properties of the 8-(3-chlorobenzylideneamino)naphthalene-1,3-disulfonic acid were studied by adding 0.2 mL DPPH (0.75 mM)) to compound 8-(3-chlorobenzylideneamino)naphthalene-1,3-disulfonic acid (III) (3 µM) in ethanol. After 30 min of incubation in the dark, the absorbance was read against a blank at 517 nm. Ascorbic acid (vitamin C) was used as standard antioxidants (positive control). A blank sample was prepared by 0.2 ml of DPPH in 3 ml ethanol. A negative control sample was run using ethanol instead of the sample. The radical scavenging inhibition was calculated using the following equation:

$$\text{Inhibition \%} = \frac{(A_{blank} - A_{sample})}{(A_{blank})} \times 100$$

The antioxidant activity for the synthesized compound is listed in Table 1, using Vitamin C as a reference.

TABLE 1

The antioxidant activity of both control and 8-(3-chlorobenzylideneamino)naphthalene-1,3-disulfonic acid

| Compound | A | Inhibition |
|---|---|---|
| Product III | 0.21 | 50 |
| blank | 0.46 | 0 |
| vit c | 0.12 | 74% |

It is to be understood that the 4-(4,5-bis(3-chlorophenyl)-2-(4-methoxyphenyl)-1H-imidazol-1-yl)benzoic acid compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An 8-(3-chlorobenzylideneamino)naphthalene-1,3-disulfonic acid compound having the formula I:

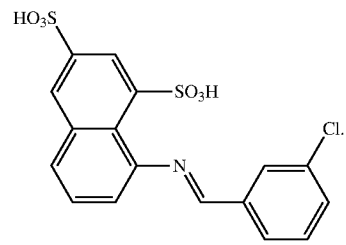

2. A pharmaceutically acceptable composition comprising a therapeutically effective amount of the 8-(3-chlorobenzylideneamino)naphthalene-1,3-disulfonic acid compound of claim 1 and a pharmaceutically acceptable carrier.

3. A method of making the 8-(3-chlorobenzylideneamino)naphthalene-1,3-disulfonic acid compound of claim 1, the method comprising:
   mixing 8-aminonaphthalene-1,3-disulfonic acid, 3-chlorobenzaldehyde, and triethylamine (TEA) in ethanol to obtain a solution;
   irradiating the solution followed by cooling to room temperature to obtain a formed precipitate;
   purifying the formed precipitate by filtering and recrystallization using ethanol; and
   obtaining the 8-(3-chlorobenzylideneamino)naphthalene-1,3-disulfonic acid compound.

4. The method of making the 8-(3-chlorobenzylideneamino)naphthalene-1,3-disulfonic acid compound of claim 3, wherein the step of irradiating the solution takes place in a sonicator for at least about 2 hours.

5. The method of making the 8-(3-chlorobenzylideneamino)naphthalene-1,3-disulfonic acid compound of claim 3, wherein the step of irradiating the solution is conducted at about 50° C.

6. The method of making the 8-(3-chlorobenzylideneamino)naphthalene-1,3-disulfonic acid compound of claim 3, wherein the step of purifying the formed precipitate includes collecting the formed precipitate by filtration and washing the formed precipitate with distilled water.

7. The method of making the 8-(3-chlorobenzylideneamino)naphthalene-1,3-disulfonic acid compound of claim 3, wherein the 8-aminonaphthalene-1,3-disulfonic acid and the 3-chlorobenzaldehyde are added in about a 1:1 molar ratio.

* * * * *